(12) United States Patent
Zilla et al.

(10) Patent No.: US 11,083,876 B2
(45) Date of Patent: Aug. 10, 2021

(54) DILATION DEVICE

(71) Applicant: TEVAR (PTY) LTD, Cape Town (ZA)

(72) Inventors: Peter Paul Zilla, Cape Town (ZA); Deon Bezuidenhout, Cape Town (ZA); Edward Charles Teddy Mudge, Cape Town (ZA)

(73) Assignee: Tevar (Pty) Ltd, Cape Town (ZA)

( * ) Notice: Subject to any disclaimer, the term of this patent is extended or adjusted under 35 U.S.C. 154(b) by 236 days.

(21) Appl. No.: 16/482,983

(22) PCT Filed: Feb. 14, 2018

(86) PCT No.: PCT/ZA2018/050010
§ 371 (c)(1),
(2) Date: Aug. 1, 2019

(87) PCT Pub. No.: WO2018/152556
PCT Pub. Date: Aug. 23, 2018

(65) Prior Publication Data
US 2019/0351199 A1   Nov. 21, 2019

(30) Foreign Application Priority Data
Feb. 15, 2017   (ZA) .................................. 2017/01122

(51) Int. Cl.
  *A61M 25/10* (2013.01)
  *A61M 29/02* (2006.01)
  *A61F 2/958* (2013.01)
(52) U.S. Cl.
  CPC .... *A61M 25/1002* (2013.01); *A61M 25/1011* (2013.01); *A61M 29/02* (2013.01);
(Continued)

(58) Field of Classification Search
  CPC ............... A61F 2/958; A61M 25/1002; A61M 25/1011; A61M 25/104; A61M 25/10;
(Continued)

(56) References Cited

U.S. PATENT DOCUMENTS

| 4,762,130 A | * | 8/1988 | Fogarty | ............ | A61M 25/1002 606/159 |
| 5,019,042 A | * | 5/1991 | Sahota | ............ | A61M 25/1002 604/101.01 |

(Continued)

FOREIGN PATENT DOCUMENTS

WO   2014030078   2/2014

OTHER PUBLICATIONS

Search report and written opinion in international application No. PCT/ZA2018/050010 dated Jul. 20, 2018.

*Primary Examiner* — Jocelin C Tanner
(74) *Attorney, Agent, or Firm* — Haugen Law Firm PLLP (57) ABSTRACT

A dilatation device 10 includes a support 14 and at least one inflatable tube 16. The inflatable tube is wound helically around the support and also defines a series of inflatable zones 26 along its length, with successive inflatable zones spaced by an intermediate zone 28 that is more resistive to radial expansion than the inflatable zones. The inflatable tube further defines a fluid inlet 22, 24 for: introducing fluid to inflate the inflatable zones; and extracting fluid from the inflatable tube to deflate it, with each inflatable zone being in fluid communication with its successive inflatable zones via the intermediate zones. The axial critical buckling load of the inflatable zones is less than the radial critical buckling load of the inflatable zones, to cause the inflatable zones to concertina axially when the inflatable tube is depressurized, thereby causing the intermediate zones to displace towards each other.

23 Claims, 10 Drawing Sheets

(52) U.S. Cl.
CPC ...... *A61F 2/958* (2013.01); *A61M 2025/1061* (2013.01); *A61M 2025/1072* (2013.01); *A61M 2025/1084* (2013.01)

(58) Field of Classification Search
CPC .......... A61M 29/02; A61M 2025/1072; A61M 2025/1084; A61M 2025/1013; A61M 2025/1015; A61M 2025/1061
See application file for complete search history.

(56) References Cited

U.S. PATENT DOCUMENTS

| | | | |
|---|---|---|---|
| 5,843,116 A * | 12/1998 | Crocker | A61M 25/1002 606/192 |
| 2002/0045925 A1* | 4/2002 | Keller | A61F 7/12 607/106 |
| 2004/0167509 A1 | 8/2004 | Taimisto | |
| 2007/0129749 A1* | 6/2007 | Thomas | A61M 25/1002 606/194 |
| 2008/0306440 A1* | 12/2008 | Hirszowicz | A61M 29/02 604/99.01 |
| 2011/0144742 A1* | 6/2011 | Madrid | A61F 2/2433 623/2.11 |
| 2012/0245520 A1 | 9/2012 | Kelly et al. | |
| 2018/0153692 A1 | 6/2018 | Zilla et al. | |

\* cited by examiner

DILATION DEVICE

BACKGROUND

The present invention relates to a dilatation device. More particularly, the present invention relates to a dilatation device including an axially collapsible helical beaded balloon.

Various Inflatable Dilatation Devices are Known. For Instance:

US2003/0176758 "Catheter for radiation therapy", US2009/0281612 "Balloon catheter stent delivery system with ridges", US2012/0059401 "Device and method for compartmental vessel treatment", US2013/0116655 "Balloon assemblies having controllably variable topographies" and US2013/0218181 "Constraining structure with non-linear axial struts" describe dilators including an inflatable tube within a rigid tubular body, wherein inflation of the inflatable tube causes portions of the inflatable tube to protrude radially through apertures defined by the rigid tubular body.

US2002/0120321 "Stent retention mechanism", US2014/0066960 "System and method for treating biological vessels", US2015/0133988 "Flexible high-pressure balloons", US2016/0022455 "Stent delivery system having dynamic deployment and methods of manufacturing same", U.S. Pat. No. 5,019,042 "Balloon catheters", U.S. Pat. No. 5,308,356 "Passive perfusion angioplasty catheter", U.S. Pat. No. 5,295,959 "Autoperfusion dilatation catheter having a bonded channel", U.S. Pat. No. 5,484,411 "Spiral shaped perfusion balloon and method of use and manufacture", U.S. Pat. No. 5,620,457 "Catheter balloon", U.S. Pat. No. 5,976,106 "Medical appliance with centering balloon" and U.S. Pat. No. 6,245,040 "Perfusion balloon brace and method of use" and describe dilatators including an inflatable tube surrounding a support rod and a radial restrictor wound about the tube to cause the tube to inflate to form bulbous segments. U.S. Pat. No. 5,308,356 further describes a set of parallel inflatable tubes located around the support and a radial restrictor wound about the tubes to cause the multi-strand catheter to form bulbous segments. A similar multi-tube dilatator is described in US2008/0097374 "Inflatable shaped balloons".

U.S. Pat. No. 5,649,978 "Temporal inflatable intravascular prosthesis" describes an inflatable tube wound to form a helix, with restraints to inhibit axial expansion of the helical tube, which inflatable tube inflates uniformly along its length when pressurised. US2012/0245520 "Spiral perfusion dilatation balloon for use in valvuloplasty procedure" further describes such an inflatable tube would about a support rod.

WO2007/012443 "Balloon dilatation catheter", US2010/0094403 "Medical device", US2010/0262124 "Spiral balloon catheter", US2012/0245520 "Spiral perfusion dilatation balloon for use in valvuloplasty procedure", U.S. Pat. No. 5,181,911 "Helical balloon perfusion angioplasty catheter", U.S. Pat. No. 5,797,948 "Centering balloon catheter" and U.S. Pat. No. 6,679,860 "Intraluminal therapy catheter with inflatable helical member and methods of use" describe dilating devices with a support rod and a single inflatable tube helically wound around the rod and secured at its axial ends to the rod, which tube inflates uniformly along its length upon pressurisation of the tube. JP2015-37605, WO2014/177893 "Expandable balloon" and U.S. Pat. No. 4,881,939 "Implantable helical cuff" further describe restraints wound about the inflatable tube to provide consecutive inflatable zones and restrained intermediate zones, which inflatable zones inflate to form bubbles between the restrained intermediate zones when the tube is pressurised. Furthermore, U.S. Pat. No. 6,450,988 "Centering catheter with improved perfusion" describes the tubes defining bulbous formations (instead of restraints), which bulbous formations project radially upon inflation of the tube.

U.S. Pat. No. 4,762,130 "Catheter with corkscrew-like balloon" describes a dilatator with a support rod and a single inflatable tube helically wound around the rod, wherein a first axial end of the tube is secured to the support rod and a second axial end of the tube is slidable along the support rod, whereupon pressurisation of the tube causes the tube to inflate uniformly along its length and the axial ends of the tube to move towards each other.

US2013/0296983 "Multiple lumen heat exchange catheters", U.S. Pat. No. 5,383,856 "Helical spiral balloon catheter" and U.S. Pat. No. 8,784,476 "Helical stent" describe dilatators with: (i) a support rod; (ii) a pair of tubes fixed to the rod at the axial ends of the tubes and wound around the rod to create a double-helix; and (iii) a manifold for pressurising the tubes, wherein the tubes inflate uniformly along their length to define a central lumen.

U.S. Pat. No. 6,527,739 "Spiralled balloon arrangement for treatment of a tortuous vessel" describes a dilatator with: (i) a support rod; (ii) a pair of tubes wound around the rod to create a double-helix; and (iii) a manifold for pressurising the tubes, wherein the wall thickness of each tube varies along its length to provide consecutive inflatable zones and intermediate zones, which inflatable zones inflate to form bubbles between the intermediate zones when the tube is pressurised.

A drawback of prior art inflatable dilatators is that, when the inflatable zones of inflated tubes are subjected to a partial vacuum, each inflatable zone collapse radially, reducing the radial protrusion of the inflatable zone from the longitudinal axis of the inflatable zone more than the longitudinal axial length of the inflatable zone.

The most relevant prior art that shows an inflatable zone of an inflated tube that is formed to collapse both radially and axially upon being exposed to a partial vacuum is U.S. Pat. No. 5,019,042 "Balloon catheters" (at FIG. 6). However, the tube described in this patent is linear (i.e. it is not wound helically, never mind coupled with a second tube to form a double-helix). As such, axial collapse of this tube does not cause a reduction in the radial dimension of the balloon catheter.

It is an object of the present invention to provide an inflatable dilatator including an inflatable tube wound into a helix, which tube provide alternating inflatable zones and intermediate zones, wherein when the inflatable zones of the inflatable tube are subjected to a partial vacuum, each inflatable zone collapse axially, reducing the longitudinal axial length of the inflatable zone more than the radial protrusion of the inflatable zone from the longitudinal axis of the inflatable zone, and wherein axial contraction of the helically wound tube causes the radial dimension of the helical dilatator to reduce.

SUMMARY OF THE INVENTION

According to a preferred embodiment of the invention, there is provided a dilatation device that includes:
   a support;
   at least one inflatable tube wound helically around the support and connected to the support at or near the axial ends of the inflatable tube, the inflatable tube defining a series of inflatable zones along its length, with successive inflatable zones spaced by an intermediate zone that is more resistive to radial expansion than the inflatable zones;

the inflatable tube defining a fluid inlet for:
(i) introducing fluid into the inflatable tube to inflate the inflatable zones; and
(ii) extracting fluid from the inflatable tube to deflate the inflatable tube, with each inflatable zone being in fluid communication with its successive inflatable zones via the intermediate zones, characterised in that the axial critical buckling load of the inflatable zones is less than the radial critical buckling load of the inflatable zones, to cause the inflatable zones to concertina axially when the inflatable tube is depressurized, thereby causing the intermediate zones to displace towards each other.

Preferably, in respect of each inflatable zone, the diameter of the inflatable zone when in a neutral condition in which the internal pressure is the same as the ambient pressure is greater than the axial length of the inflatable zone in the neutral condition.

Typically, the dilatation device further includes second and third inflatable tubes wound helically around the support and connected to the support at or near the axial ends of the second and third inflatable tubes.

Preferably, the ratios:
$E^I$:H should be between 3:1 and 6:1
$E^I$:A-D should be between 1:1.4 and 3.33:1
A-G:A-D should be between 1.07:1 and 1.4:1
where:
$E^I$ is the outer diameter of the inflatable zones;
H is the outer diameter of the intermediate zones;
A-D is the axial length of an inflatable zone; and
A-G is the axial length of an inflatable zone plus the axial length of an intermediate zone.

Generally, each inflatable zone comprises a pair of axial end regions and an intermediate axial central region. The axial length of the axial central region may be less than or equal to the axial length of the axial end regions. Preferably, the average wall thickness of the inflatable zone in each of the axial end regions is at least 100% greater than the average wall thickness of the inflatable zone in the axial central region, thereby providing inflatable zones with an axial critical buckling load less than its radial critical buckling load.

Alternatively, each inflatable zone comprises a pair of axial end regions and an intermediate axial central region, which axial end regions are made of a first material and the axial central region is made of a second material, wherein the Young's modulus of the first material is at least double the Young's modulus of the second material, thereby providing inflatable zones with an axial critical buckling load less than its radial critical buckling load.

Further alternatively, each inflatable zone, when in the neutral condition, comprises a pair of radially extending or conical axial end regions and an intermediate axial central region that is right circular cylindrical in shape, wherein the average wall thickness of the axial end regions is at least 100% greater than the average wall thickness of the axial central region.

Even further alternatively, each inflatable zone includes at least two stiffener rings with an outer diameter greater than the outer diameter of the intermediate zones, which stiffener rings are shaped so as to have a radial critical buckling load greater than the axial critical buckling load of the inflatable zone, thereby providing inflatable zones with an axial critical buckling load less than their radial critical buckling load. The stiffener rings may be secured to the inflatable zones of the inflatable tubes, or they may be formed integrally with the inflatable zones of the inflatable tubes.

Generally, the average wall thickness of each intermediate zone is at least 200% greater than the wall thickness at the axial centre of the inflatable zones. More preferably, the average wall thickness of each intermediate zone is at least 300% greater than the wall thickness at the axial centre of the inflatable zones Optionally, a collar may be associated with each intermediate zone, which collars inhibit radial expansion of the intermediate zones in the region of the collars during inflation of the inflatable tube, and radial collapse of the intermediate zones in the region of the collars during deflation of the inflatable tube under partial vacuum.

Typically: (i) each inflatable zone is between 3 mm and 8 mm in axial length when in the neutral condition; and (ii) each intermediate zone is between 0.5 mm and 2 mm in axial length.

Generally, the support is a rod that defines a longitudinal bore with open axial ends.

Preferably, the dilatation device further includes a locating tube that defines a pair of longitudinally extending co-axial bores, wherein the support extends axially from a first axial end of the locating tube.

Typically: (i) the outer co-axial bore defined by the locating tube is in fluid communication with the inlet of each inflatable tube, in use to vary fluid volume within each inflatable tube; and (ii) a guidewire lies within the support, which in turn is located within the locating tube, and extends along a central bore defined by the support. Importantly, the central bore defined by the support is not in fluid communication with either the bore defined by the locating tube or the inflatable tubes.

Generally, the dilatation device further includes a manifold that provides fluid communication between the outer co-axial bore defined by the locating tube and the fluid inlet of each inflatable tube.

Preferably, the dilatation device further includes at least one tie that extends helically about the support and inflatable tubes in a direction opposite to the helix formed by the inflatable tubes. Alternatively, the dilatation device further includes at least one shackle that connects intermediate zones of adjacent inflatable tubes. Further alternatively, an intermediate zone on a first inflatable tube is bonded to an adjacent intermediate zone of a second inflatable tube. Even further alternatively, an inflatable zone on a first inflatable tube is bonded to an adjacent inflatable zone on a second inflatable tube.

Typically, the dilatation device further includes means for pressurizing fluid within the outer co-axial bore defined by the locating tube, which pressurizing means, in use, varies pressure within the fluid between 0.1 atmospheres and 4 atmospheres absolute pressure.

BRIEF DESCRIPTION OF THE DRAWINGS

The invention will now be described in more detail, by way of examples only, with reference to the accompanying drawings in which.

DESCRIPTION OF THE INVENTION

With reference to FIGS. 1 to 7 of the drawings, a dilatation device 10 according to a preferred embodiment of the invention is provided for dilating vessels and stents. The dilatation device 10 includes a locating tube 12, a support 14 and three inflatable tubes 16 would helically about the support 14.

The locating tube 12 is an elongate hollow tube between 900 mm and 1200 mm in axial length, which defines co-axial bores—a central bore 18; and an outer bore 20—that extend between the first and second axial ends 12a and 12b, respectively, of the locating tube 12. However, the outer bore 20 terminates prior to the second axial end 12b of the locating tube 12. The locating tube 12 is sufficiently flexible, in use, to permit the locating tube 12 to be inserted into and pass along a non-linear artery, and sufficiently strong to resist hoop stresses resulting from pressurisation of fluid within the locating tube 12 bores 18 and 20. Preferably, the locating tube 12 is made of a polymer such as a polyurethane, Nylon or PEBAX™. The locating tube 12 defines: a first inlet 22 at or near the second axial end 12b of the locating tube 12 that facilitates control of a guidewire that extends along the locating tube 12; a second inlet 24 at or near the second axial end 12b of the locating tube 12 that permits fluid communication with the outer bore 20 defined by the locating tube 12; a first outlet from the central bore 18 at or near the first axial end 12a of the locating tube 12; and a second outlet from the outer bore 20 at or near the second axial end 12b of the locating tube 12. Typically, the support 14 extends from the first inlet 22, along the outer bore 20; and the guidewire extends along the central bore 18 defined by the support 14. Importantly, the central bore 18 defined by the support 14 is not in fluid communication with either the outer bore 20 defined by the locating tube 12 or the inflatable tubes 16.

The first and second inlets 22 and 24 are provided by apertures defined by the radial wall of the locating tube 12 near the second axial end 12b of the locating tube 12. The first and second outlets of the locating tube 12 are provided by apertures defined by the first axial end 12a of the locating tube 12. Although references are made to second inlet 24 and second outlet, it will be appreciated that, although: the second inlet 24 permits fluid to enter the outer bore 20; and the outlet permits fluid to exit the outer bore 20, during inflation/pressurisation of the dilatation device 10, during deflation/depressurisation of the dilatation device 10, the fluid flow is reversed, i.e.: the second inlet 24 permits fluid to exit the outer bore 20; and the outlet permits fluid to enter the outer bore 20.

It will be appreciated that the inflatable zones 26 may be made of a very compliant material, requiring a minimal: increase in pressure consequent to an internal volumetric increase to inflate the inflatable zones 26; and decrease in pressure consequent to an internal volumetric decrease to deflate the inflatable zones 26.

The support 14 is in the form of a rod that defines a longitudinal bore with open axial ends. Preferably, the support 14 is made of a polymer such as polyurethane, Nylon or PEBAX™, which could be braid-reinforced. A first axial end of the support 14 defines an outlet from the longitudinal bore defined by the support 14 and a second axial end of the support 14 is connected to, and extends axially from the first axial end 12a of the locating tube 12. The longitudinal bore defined by the support 14 extends from the central bore 18 outlet defined by the locating tube 12 to permit a guidewire to extend therethrough.

The three inflatable tubes 16 are wound helically about the support 14 (i.e. in the shape of a circular helix) and connected to the support 14 at or near the axial ends of the inflatable tubes 16. Each inflatable tube 16 defines a closed axial first end and an open axial second end, which open axial second end is herein referred to as the inflatable tube 16 fluid inlet. The inflatable tube 16 fluid inlets are connected to, and in fluid communication with the outer bore 20 outlet defined by the locating tube 12 via a manifold 23. The manifold 23 also ensures equi-pressurisation/equi-inflation/equi-depressurisation/equi-deflation of the inflatable tubes 16. Although not shown, it will be appreciated that each inflatable tube 16 could alternatively, define an inflatable tube 16 fluid inlet at each axial end of the inflatable tube 16 (i.e. wherein the inflatable tube 16 is open at both axial ends). The inflatable tube 16 fluid inlets could in this alternative arrangement be connected to, and be in fluid communication with the outer bore 20 outlet defined by the locating tube 12 via manifolds. Providing a fluid inlet at each axial end of the inflatable tube 16 facilitates depressurisation of the inflatable tube (i.e. if the passage of fluid to one of the fluid inlets is blocked, the fluid may flow to, and exit the inflatable tube 16 via the other fluid inlet).

Figure 5:
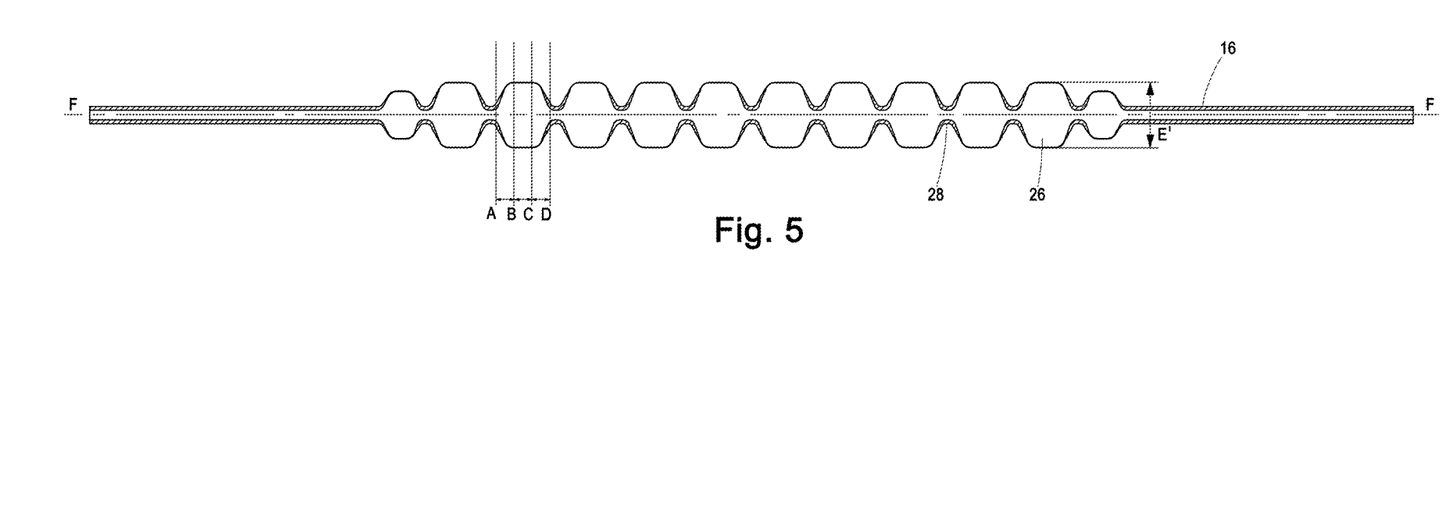
FIG. 5 is a cross-sectional side view of an inflatable tube of the dilatation device in FIG. 1, with the inflatable tubes in a neutral condition (i.e. with the internal pressure the same as the external pressure)
Figure 6:
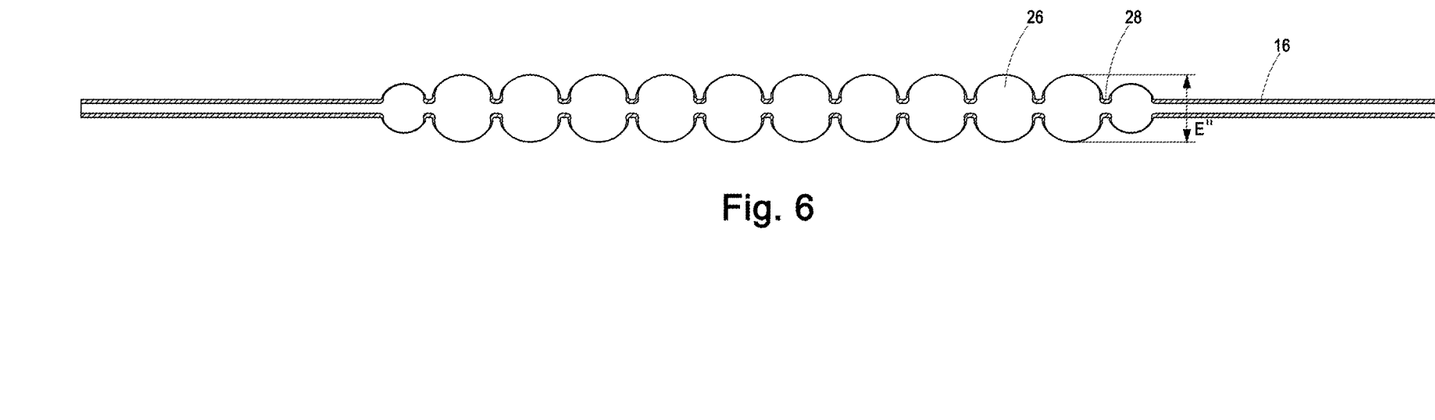
FIG. 6 is a cross-sectional side view of the inflatable tube in FIG. 5, with the inflatable tube in an inflated condition.

Each inflatable tube 16 comprises/defines a series of inflatable zones 26 along its length, with successive inflatable zones 26 spaced by an intermediate zone 28. The inflatable zones 26 and intermediate zones 28 are in fluid communication with each other. The intermediate zones 28 are more resistive to radial expansion than the inflatable zones 26, such that internal fluid volumetric increase/pressurisation of the interior of the inflatable tubes 16 causes the inflatable zones 26 radially to inflate more than the intermediate zones 28. Typically: each inflatable zone 26 is between 3 mm and 8 mm in axial length when in the neutral condition; and each intermediate zone 28 is between 0.5 mm and 2 mm in axial length. Preferably, the average wall thickness of each intermediate zone 28 is at least 200% greater than the wall thickness at the axial centre of the inflatable zones 26. More preferably, the average wall thickness of each intermediate zone 28 is at least 300% greater than the wall thickness at the axial centre of the inflatable zones 26.

Figure 7:
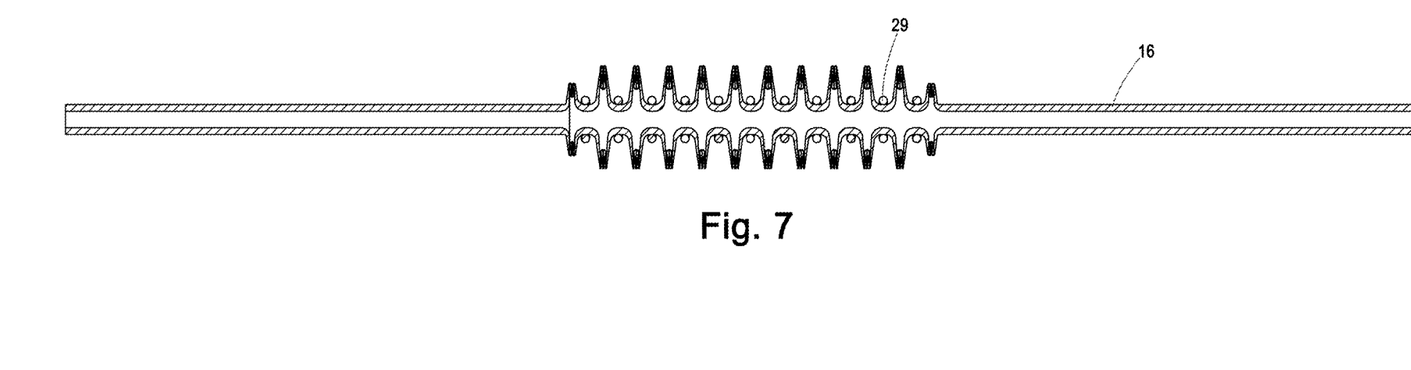
FIG. 7 is a cross-sectional side view of the inflatable tube in FIG. 5 including collars about the intermediate zones, with the inflatable tube in a collapsed condition.

Further to inhibit radial inflation of the intermediate zones 28 during internal fluid volumetric increase/pressurization of the inflatable tubes 16, a collar 29 may optionally be associated with each intermediate zone 28. The collar 29 may be formed within the intermediate zone 28 or (as shown in FIG. 7), the collar 29 may be located radially about the intermediate zone 28. The collars 29 inhibit radial expansion of the intermediate zones 28 in the region of the collars 29 during inflation of the inflatable tube 16, and radial collapse of the intermediate zones 28 in the region of the collars 29 during deflation of the inflatable tube 16 under partial vacuum.

FIG. 5 shows an inflatable tube 16 (shown as a linear tube instead of a helical tube for ease of representation) in a neutral condition, i.e. where the internal pressure is the same as the external/ambient pressure. Each inflatable zone 26 can be divided into three regions—two axial end regions A-B and C-D separated by an intermediate axial central region B-C. The axial length of the axial central region B-C may be less than or equal to the axial length of the axial end regions A-B and C-D. However, the axial central region B-C and the axial end regions A-B and C-D are preferably of equi-axial length. The average wall thickness of the axial end regions A-B and C-D is at least 100% greater than the average wall thickness of the axial central region B-C. The greater wall thickness of the axial end regions A-B and C-D cause the radial critical buckling load of the inflatable zones 26 to be more than the axial critical buckling load of the inflatable zones 26. With such a property (i.e. the axial critical buckling load being less than the radial critical buckling load), when the inflatable zones 26 are subjected to internal fluid volumetric decrease/negative pressure (i.e. internal pressure less than external/ambient pressure), the internal fluid volumetric decrease/negative pressure causes buckling of the axial central region B-C(e.g. in a concertina fashion) before material radial buckling of the axial end regions A-B and C-D. In other words, internal fluid volumetric decrease/negative pressure causes the inflatable zones 26 to collapse primarily axially instead of primarily radially, thereby causing the intermediate zones 28 to displace towards each other and the axial length of the inflatable tube 16 to shorten. When wound in a helical manner, this shortening has the benefit of producing a small outer diameter (G) when under vacuum.

It has been found that to facilitate axial collapse of the inflatable zones 26, in respect of each inflatable zone 26, the diameter ($E^I$ shown in FIG. 5) of the inflatable zone 26 in the neutral condition should be greater than the axial length (A-B-C-D shown in FIG. 5) of the inflatable zone 26 in the neutral condition.

Further alternatively, instead of the average wall thickness of the pair of axial end regions A-B and C-D being greater than the average wall thickness of the intermediate axial central region B-C, the axial end regions A-B and C-D could be made of a first material and the axial central region B-C could be made of a second material, wherein the Young's modulus of the first material is at least double Young's modulus of the second material. By increasing the Young's modulus of the axial end regions A-B and C-D relative to the axial central region B-C, the radial critical buckling load of the inflatable zones 26 is increased beyond its axial critical buckling load.

Remaining with FIG. 5, each intermediate zone 28 of the inflatable tubes 16 have an axial length of D-G and an outer diameter (H). To induce concertina of the inflatable zones 26, ratios:
$E^I$:H should be between 3:1 and 6:1
$E^I$:A-D should be 1:1.14 and 3.33:1
A-G:A-D should be 1.07:1 and 1.4:1

Furthermore, according to a slight variation (not specifically shown) of the preferred embodiment described above, each inflatable zone 26, when in a neutral condition, comprises a pair of radially extending or conical axial end regions and an intermediate axial central region that is right circular cylindrical in shape, wherein the average wall thickness of the axial end regions is at least 100% greater than the average wall thickness of the axial central region.

Figure 1:
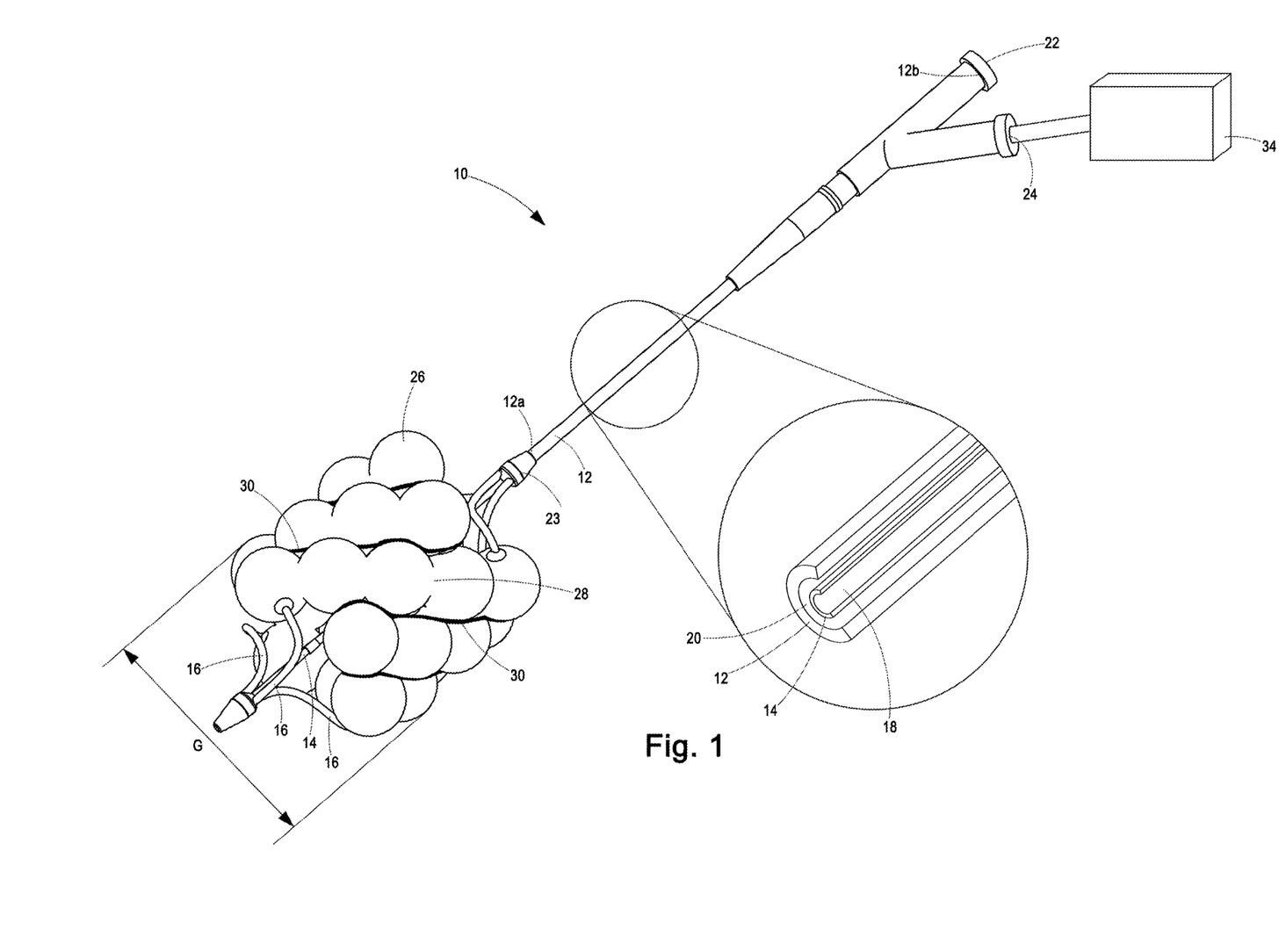
FIG. 1 is a perspective view of a dilatation device according to a preferred embodiment of the invention, with the flexible tubes in an inflated condition.
Figure 2:
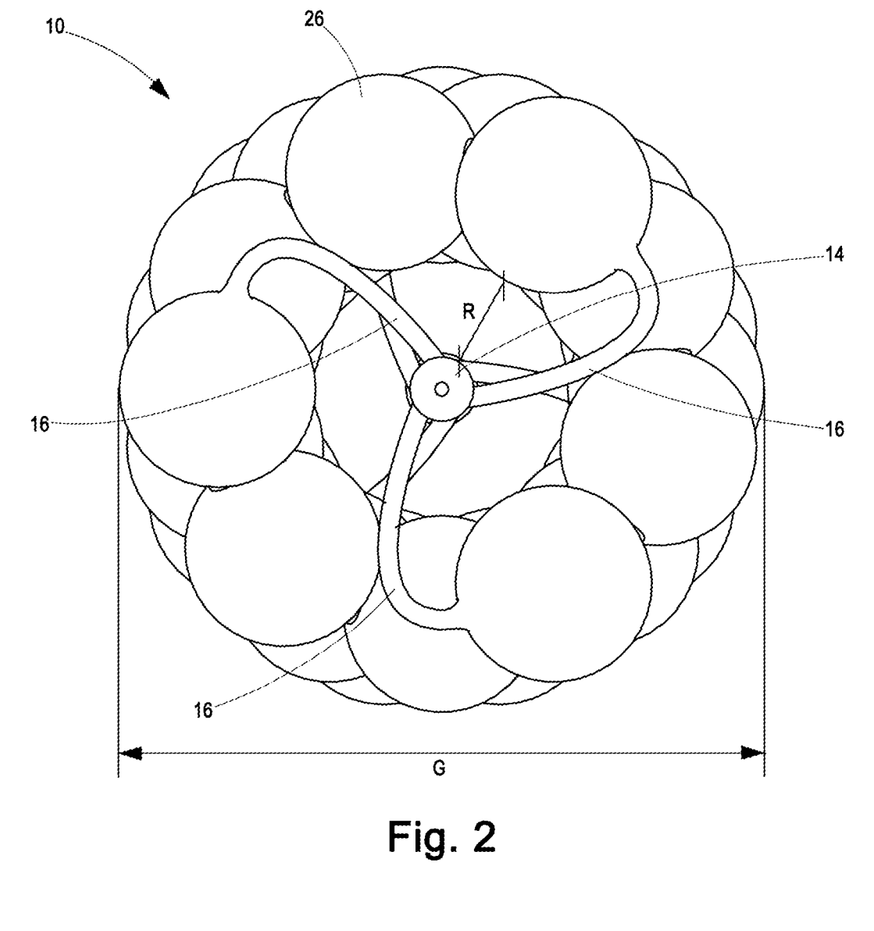
FIG. 2 is an axial view of the dilatation device in FIG. 1, with the flexible tubes in the inflated condition.
Figure 3:
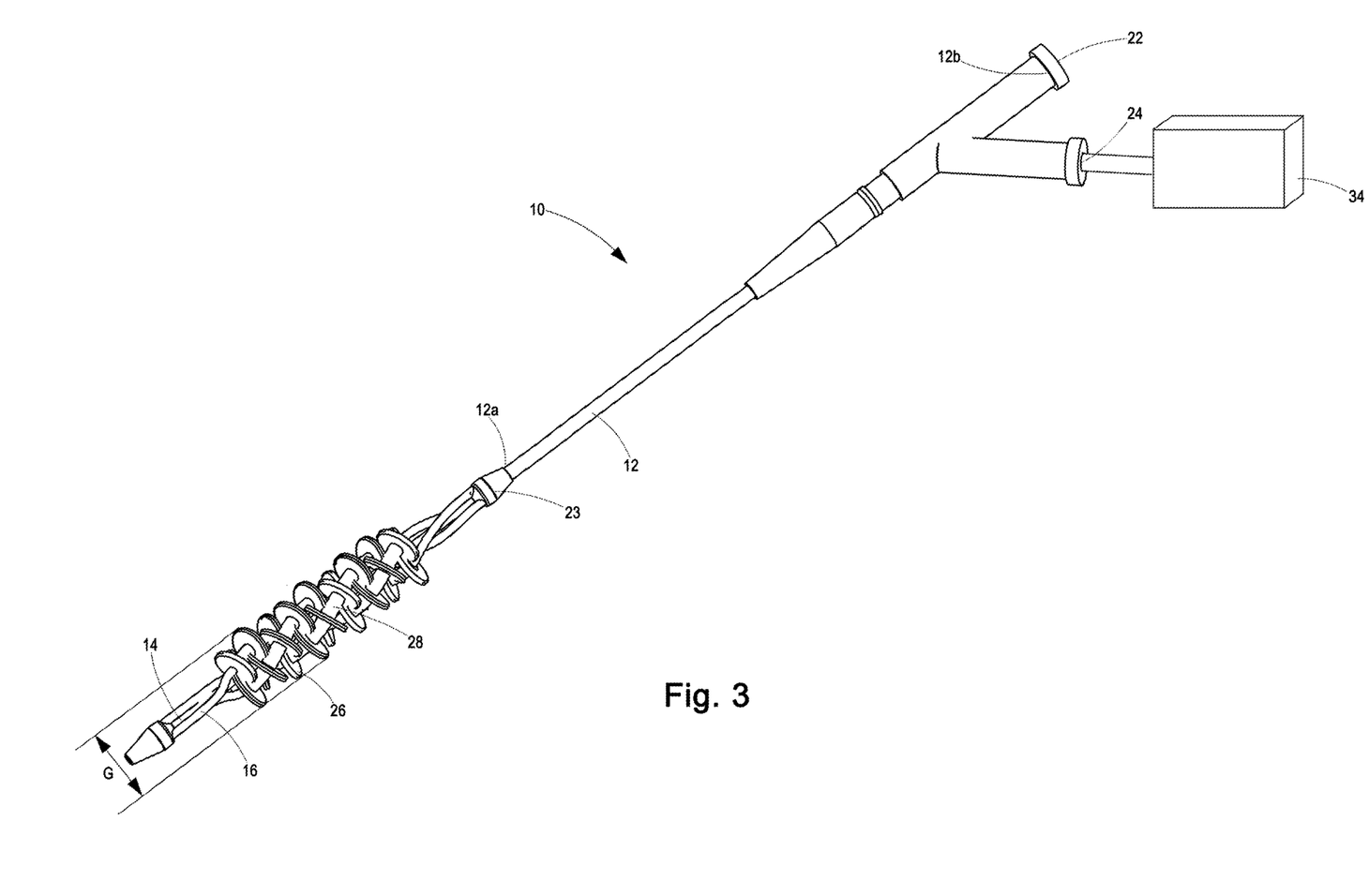
FIG. 3 is a perspective view of the dilatation device in FIG. 1, with the flexible tubes in a collapsed condition.
Figure 4:
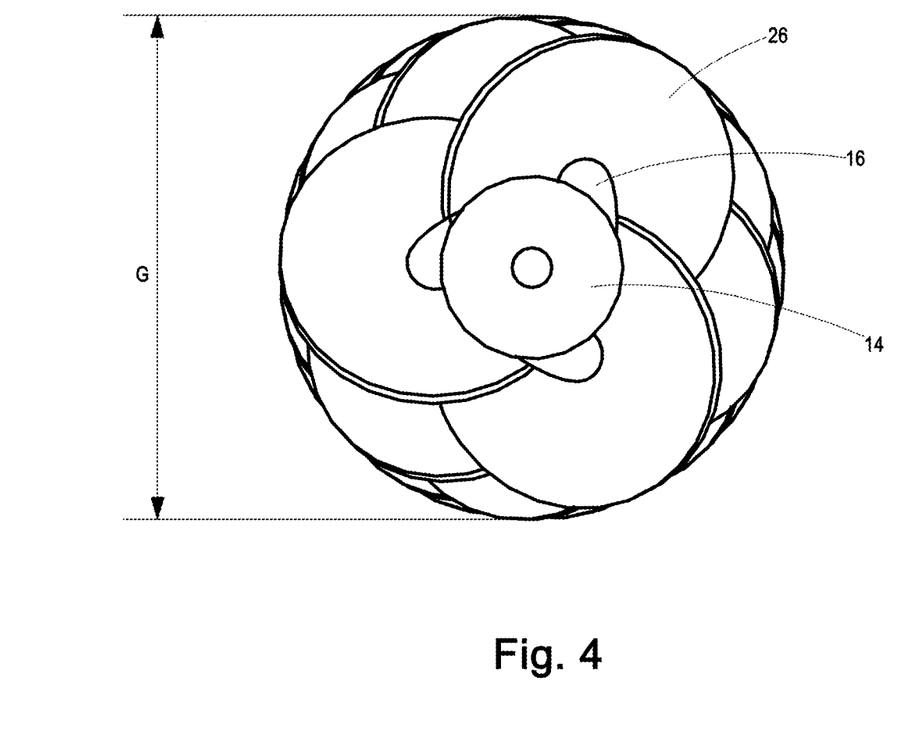
FIG. 4 is an axial view of the dilatation device in FIG. 1, with the flexible tubes in the collapsed condition.

Returning to the preferred embodiment shown in FIGS. 1 to 7, initially, the inflatable tube 16 is in the neutral condition shown in FIG. 5. Upon internal fluid volumetric increase/pressurization of the interior of the inflatable tube 16, the inflatable zones 26 radially inflate to an inflated condition shown in FIG. 6. Turning to FIG. 2, when in the inflated condition, the inflatable zones 26 define a central lumen with radius R to facilitate flow of blood therethrough. Subsequent internal fluid volumetric decrease/depressurization of the inflatable tube 16 to a pressure less than external/ambient pressure causes the inflatable zones 26 to collapse to a collapsed condition shown in FIGS. 3, 4 and 7.

Figure 10:
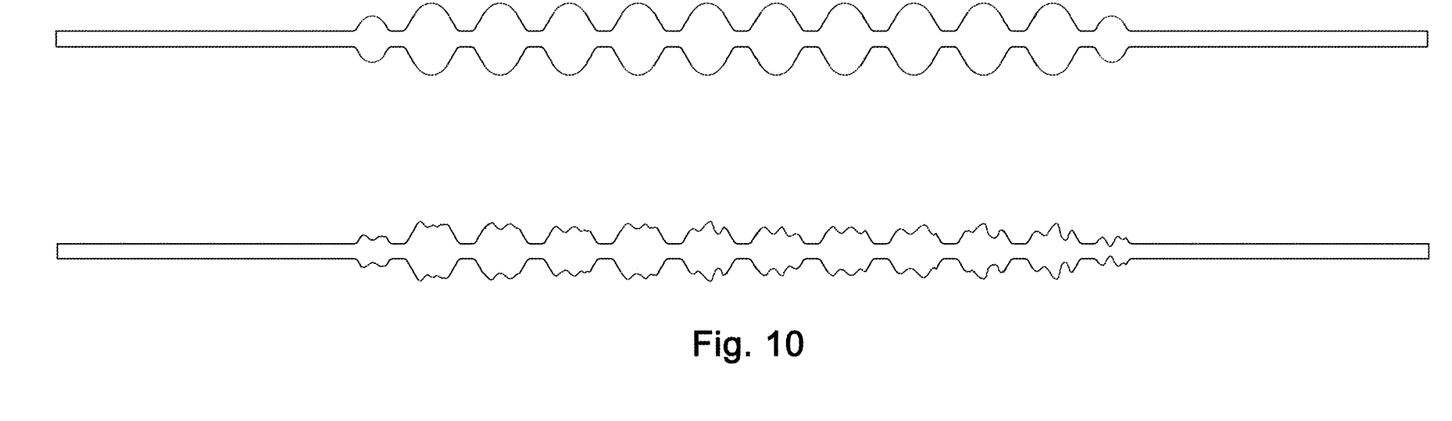
FIG. 10 are side views of a typical radially collapsing inflatable tube according to the prior art in: (i) an inflated condition; and (ii) a collapsed condition.

Axial collapse of the inflatable zones 26 causes greater radial contraction of the helically wound inflatable dilatation device 10 than radial collapse of the inflatable zones 26. Prior art dilatation devices 10, of which an example is shown in FIG. 10, provided for radial collapse of the inflatable zones. Intuitively radial collapse of inflatable zones makes sense, as radial collapse has a direct impact on the diameter of the helix formed by the inflatable tubes 16. However, it has been found that a greater reduction in helical diameter (G) is achieved by axial contraction of the inflatable tubes 16 consequent to axial collapse of the inflatable zones 26. In other words, radial contraction of the helix formed by the inflatable tubes 16 indirectly via axial collapse of the inflatable zones 26 is preferable to radial contraction of the helix formed by the inflatable tubes directly via radial collapse of the inflatable zones. Provided that:
(i) the radial spacing of the radial inner surface of the inflatable zones 26 (when in the inflated condition) from the radial peripheral surface of the support 14 (shown as R in FIG. 2) is greater than the radius of the inflatable zones 26 (i.e. [$E^{II}$ shown in FIG. 6]/2);
(ii) deflation/depressurization of the axially collapsing inflatable zones 26 to the collapsed condition causes the inflatable tubes 26 to become tightly wound about the radial periphery of the support 14,
a dilatation device 10 with axially collapsing inflatable zones 26 will outperform (i.e. collapse to a smaller helical diameter (D)) than a similar dilatation device with radially collapsing inflatable zones.

In other words, the dilatation device 10 is particularly suited to applications where a central lumen is required to facilitate blood flow while the inflatable zones are in the inflated condition According to the preferred embodiment of the invention, the dilatation device 10 includes:
(i) inflatable zones 26 that expand from a diameter ($E^I$ shown in FIG. 5) of 7 mm in the neutral condition (at a pressure of 0 atm) to a diameter ($E^{II}$ shown in FIG. 6) of 14 mm in the inflated condition (at a pressure of 4 atm) as the internal fluid volume within the inflatable tube 26 is increased by between 200% and 350%

(ii) intermediate zones 28 1 mm in axial length;

(iii) a helical pitch of 12 mm in the inflated condition; and (iv) a helical diameter (G) of 40 mm in the inflated condition Axial collapse of the inflatable zones 26/axial shortening of the inflatable tubes 16 during internal fluid volumetric decrease/depressurization of the inflatable tubes 16 causes the longitudinal axis of the inflatable tubes 16 to move radially towards the helical axis/the longitudinal axis of the support 14. This "tightening" of the helix: renders the helical inflatable tubes 16 less susceptible to "snagging" during axial movement of the dilatation device 10 along a vessel (while in the collapsed condition); and facilitates insertion of the inflatable tubes 16 into and extraction of the inflatable tubes 16 out of the body through a sheath or port (not shown).

Figure 9:
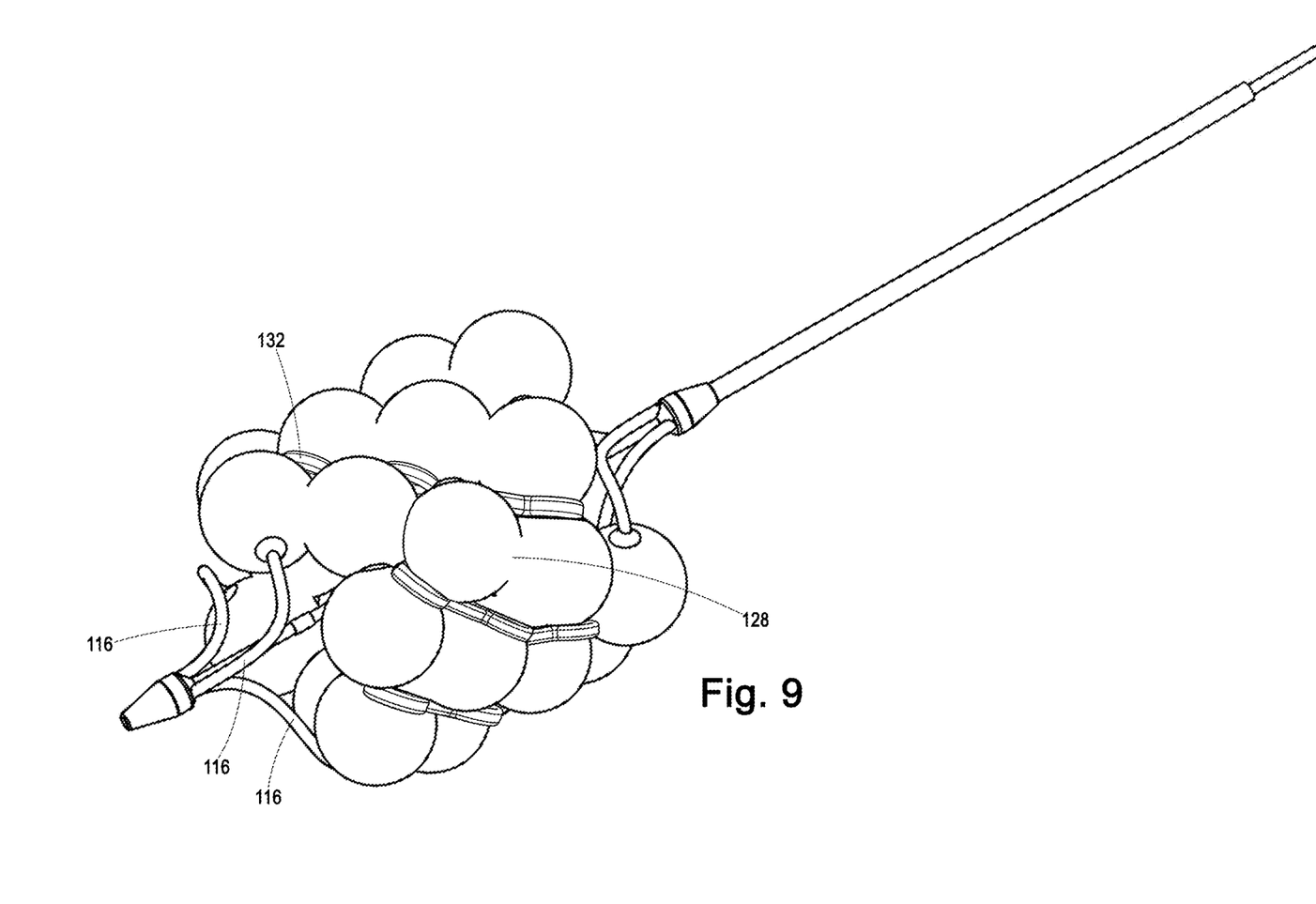
FIG. 9 is a perspective view of a dilatation device according to an alternative embodiment of the invention, with shackles connecting intermediate zones of adjacent inflatable tubes.

To maintain the relative position of the helical inflatable tubes 16 during internal fluid volumetric increase/pressurization of the inflatable tubes 16, ties 30 extend helically about the support 14 and inflatable tubes 16 in a direction opposite to the helix formed by the inflatable tubes 16 (e.g. if the inflatable tubes 16 are wound in a right handed helix, the ties 30 are wound in a left handed helix, and vice versa). As an alternative to ties 30, intermediate zones 128 of adjacent inflatable tubes 116 could be connected to each other via shackles 132, as shown in FIG. 9. Further alternatively, but not shown, instead of employing ties 30 and/or shackles 132 an intermediate zone on a first inflatable tube may be bonded directly to an adjacent intermediate zone of a second inflatable tube. Even further alternatively, an inflatable zone 26 on a first inflatable tube 16 is bonded to an adjacent inflatable zone 26 on a second inflatable tube 26.

Returning to the preferred embodiment in FIGS. 1 to 7, the dilatation device 10 also includes means 34 for varying the fluid flow/pressure of fluid within the outer axial bore 20 defined by the locating tube 12 between 0.1 atmospheres and 4 atmospheres absolute pressure.

Figure 8:
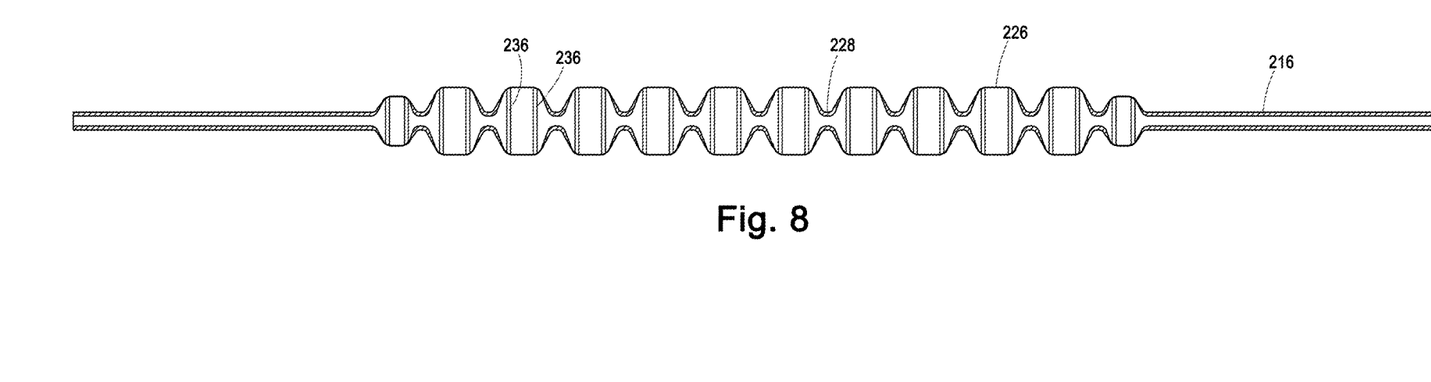
FIG. 8 is a cross-sectional side view of an alternative embodiment of the inflatable tube, with each inflatable zone including a pair of stiffener rings.

Although FIGS. 1 to 7 describe a preferred embodiment that uses a variation in inflatable tube 16 wall thickness to cause the radial critical buckling load of the inflatable zones 26 to be greater than the axial critical buckling load of the inflatable zones 26, it will be appreciated that other arrangements to achieve such characteristic/property (i.e. the radial critical buckling load of the inflatable zones 26 being more than the axial critical buckling load of the inflatable zones 26) are possible. For instance, FIG. 8 shows an alternative embodiment of the inflatable tube 216 (shown as a linear tube instead of a helical tube for ease of representation). The inflatable tube 216 according to this alternative embodiment differs from the inflatable tube 16 according to the preferred embodiment in that each inflatable zone 226 of the alternative inflatable tube 216 includes a pair of stiffener rings 236. The stiffener rings 236 have an outer diameter greater than the outer diameter of the intermediate zones 228, and are axially spaced from each other. The stiffener rings 236 are also shaped so that their resistance to radial deformation (i.e. their radial critical buckling load) is greater than the resistance of the inflatable zones 226 to axial deformation (i.e. their axial critical buckling load), thereby providing the inflatable zones 226 with an axial critical buckling load less than its radial critical buckling load. For example, the radial thickness of the stiffener rings 236 could be greater than the radial wall thickness of the inflatable zone 226. The stiffener rings 236 could be secured/adhered to the inflatable tubes 216 in the vicinity of the inflatable zones 226. However, it is preferred to form the stiffener rings 236 integrally with the inflatable tube 216.

In use:

The dilatation device 10 is inserted into a vessel (directed along a guidewire that extends along the central bore 18 defined by the support 14)—first axial end of the support first—with the inflatable tubes 16 wound helically about the support 14 and in a neutral condition. Optionally, a crimped stent or stent graft may surround the helically wound inflatable tubes 16.

The support 14 with helically wound inflatable tubes 16 is threaded along the vessel to a predetermined position along the vessel.

The pressure varying means 34 is then operated to inject fluid into the outer bore 20 defined by the locating tube 12 via the second inlet 24. This injection of fluid increases the fluid pressure within such outer bore 20 and within the inflatable tubes 16 to no more than 4 atm. This internal fluid volumetric increase/pressurization of the inflatable tubes 16 causes the inflatable zones 26 to inflate radially and axially and thereby cause the helically wound inflatable tubes 16 to inflate from the neutral condition to the inflated condition, thereby dilating the vessel/surrounding stent or stent graft and defining an inner lumen for fluid flow.

After dilating the vessel/deploying the stent or after dilating the stent graft, the pressure varying means 34 is operated to extract fluid from/reduce the pressure within the outer bore 20 defined by the locating tube 12 and the pressure within the inflatable tubes 16 to as little as 0.1 atmospheres absolute pressure. This internal fluid volumetric decrease/depressurization of the inflatable tubes 16 causes the helically wound inflatable tubes 16 to move from the inflated condition to the collapsed condition. In so doing, the axial length (measured along axis F-F shown in FIG. 5) of each inflatable tube 16 is effectively reduced, thereby causing the diameter (G) of the helix formed thereby to reduce.

With the diameter (G) of the helix formed by the inflatable tubes 16 reduced, the support 14 with helically wound inflatable tubes 16 is threaded back along the vessel and removed therefrom.

The invention claimed is:

1. A dilatation device including:

a support;

at least one inflatable tube wound helically around the support and connected to the support at or near the axial ends of the at least one inflatable tube, the at least one inflatable tube defining a series of inflatable zones along its length, with successive inflatable zones spaced by an intermediate zone that is more resistive to radial expansion than the inflatable zones;

the at least one inflatable tube defining a fluid inlet for:

(i) introducing fluid into the at least one inflatable tube to inflate the inflatable zones; and (ii) extracting fluid from the at least one inflatable tube to deflate the inflatable tube, with each inflatable zone being in fluid communication with its successive inflatable zones via the intermediate zones, characterised in that an axial critical buckling load of the inflatable zones is less than a radial critical buckling load of the inflatable zones, to cause the inflatable zones to concertina axially when the at least one inflatable tube is depressurized, thereby causing the intermediate zones to displace towards each other.

2. The dilatation device according to claim 1, wherein, in respect of each inflatable zone, the diameter of the inflatable zone when in a neutral condition in which an internal pressure is the same as an ambient pressure is greater than the axial length of the inflatable zone in the neutral condition.

3. The dilation device according to claim 2, further including second and third inflatable tubes wound helically around the support and connected to the support at or near the axial ends of the second and third inflatable tubes.

4. The dilation device according to claim 3, wherein the ratios:
$E^I$:H should be between 3:1 and 6:1
$E^I$:A-D should be between 1:1.4 and 3.33:1
A-G:A-D should be between 1.07:1 and 1.4:1
where:
$E^I$ is the outer diameter of the inflatable zones;
H is the outer diameter of the intermediate zones;
A-D is the axial length of an inflatable zone; and
A-G is the axial length of an inflatable zone plus the axial length of an intermediate zone.

5. The dilatation device according to claim 4, wherein each inflatable zone comprises a pair of axial end regions and an intermediate axial central region, wherein:
(i) the axial length of the axial central region is less than or equal to the axial length of the axial end regions; and
(ii) an average wall thickness of the inflatable zone in each of the axial end regions is at least 100% greater than the average wall thickness of the inflatable zone in the axial central region, thereby providing inflatable zones with an axial critical buckling load less than its radial critical buckling load.

6. The dilatation device according to claim 4, wherein each inflatable zone comprises a pair of axial end regions and an intermediate axial central region, which axial end regions are made of a first material and the axial central region is made of a second material, wherein the Young's modulus of the first material is at least double the Young's modulus of the second material, thereby providing inflatable zones with an axial critical buckling load less than its radial critical buckling load.

7. The dilatation device according to claim 4, wherein each inflatable zone, when in the neutral condition, comprises a pair of radially extending or conical axial end regions and an intermediate axial central region that is right circular cylindrical in shape, wherein the average wall thickness of the axial end regions is at least 100% greater than the average wall thickness of the axial central region.

8. The dilatation device according to claim 4, wherein each inflatable zone includes at least two stiffener rings with an outer diameter greater than the outer diameter of the intermediate zones, which stiffener rings are shaped so as to have a radial critical buckling load greater than the axial critical buckling load of the inflatable zone, thereby providing inflatable zones with an axial critical buckling load less than their radial critical buckling load.

9. The dilatation device according to claim 8, wherein the stiffener rings are secured to the inflatable zones of the inflatable tubes.

10. The dilatation device according to claim 8, wherein stiffener rings are integrally formed with the inflatable zones of the inflatable tubes.

11. The dilatation device according to claim 1, wherein the average wall thickness of each intermediate zone is at least 200% greater than the wall thickness at the axial centre of the inflatable zones.

12. The dilatation device according to claim 1, wherein the average wall thickness of each intermediate zone is at least 300% greater than the wall thickness at the axial centre of the inflatable zones.

13. The dilatation device according to claim 12, wherein: (i) each inflatable zone is between 3 mm and 8 mm in axial length when in the neutral condition; and (ii) each intermediate zone is between 0.5 mm and 2 mm in axial length.

14. The dilatation device according to claim 13, wherein the support is a rod that defines a longitudinal bore with open axial ends.

15. The dilatation device according to claim 14, further including a locating tube that defines a pair of longitudinally extending co-axial bores, wherein the support extends axially from a first axial end of the locating tube.

16. The dilatation device according to claim 14, wherein: (i) an outer co-axial bore defined by a locating tube is in fluid communication with the inlet of each inflatable tube, in use to vary fluid volume within each inflatable tube; and (ii) a guidewire extends along the locating tube.

17. The dilatation device according to claim 16, further including a manifold that provides fluid communication between the outer co-axial bore defined by the locating tube and the fluid inlet of each inflatable tube.

18. The dilatation device according to claim 17, further including at least one tie that extends helically about the support and the at least one inflatable tube in a direction opposite to the helix formed by the at least one inflatable tube, for securing adjacent inflatable tubes together.

19. The dilatation device according to claim 18, further including means for pressurizing fluid within the outer co-axial bore defined by the locating tube, which pressurizing means, in use, varies pressure within the fluid between 0.1 atmospheres and 4 atmospheres absolute pressure.

20. The dilatation device according to claim 17, further including at least one shackle that connects intermediate zones of adjacent inflatable tubes.

21. The dilatation device according to claim 17, wherein an intermediate zone on a first inflatable tube is bonded to an adjacent intermediate zone of a second inflatable tube.

22. The dilatation device according to claim 17, wherein an inflatable zone on a first inflatable tube is bonded to an adjacent inflatable zone on a second inflatable tube.

23. The dilatation device according to claim 1 further including a collar associated with each intermediate zone, which collars inhibit radial expansion of the intermediate zones in a region of the collars during inflation of the inflatable tube, and radial collapse of the intermediate zones in the region of the collars during deflation of the inflatable tube under partial vacuum.

\* \* \* \* \*